United States Patent [19]

Suzuki et al.

[11] Patent Number: 4,682,981
[45] Date of Patent: Jul. 28, 1987

[54] MEDICAL DEVICE

[75] Inventors: Tatsuo Suzuki, Machida; Atsushi Matsumoto, Fuji, both of Japan

[73] Assignee: Terumo Kabushiki Kaisha, Tokyo, Japan

[21] Appl. No.: 762,613

[22] Filed: Aug. 5, 1985

[30] Foreign Application Priority Data

Aug. 7, 1984 [JP] Japan ................. 59-165452

[51] Int. Cl.$^4$ ........................................... A61M 29/00
[52] U.S. Cl. ................................. 604/158; 604/104; 604/165; 604/283
[58] Field of Search ................ 604/104, 107, 165, 43, 604/44, 45, 283, 158, 164, 167, 169

[56] References Cited

U.S. PATENT DOCUMENTS

| 3,399,674 | 9/1968 | Pannier et al. | |
|---|---|---|---|
| 3,633,579 | 1/1972 | Alley et al. | 604/165 |
| 3,788,320 | 1/1974 | Dye | 604/165 |
| 3,856,009 | 12/1974 | Winnie | |
| 4,192,306 | 3/1980 | Genese | 604/165 |
| 4,300,553 | 11/1981 | Seberg | 604/165 |
| 4,445,893 | 5/1984 | Bodicky | 604/165 |
| 4,493,708 | 1/1985 | Sugisawa | 604/165 |
| 4,496,348 | 1/1985 | Genese et al. | 604/169 |

FOREIGN PATENT DOCUMENTS

| 0064212 | 11/1982 | European Pat. Off. |
| 2305640 | 8/1974 | Fed. Rep. of Germany |
| 2474317 | 7/1981 | France |
| 8102098 | 8/1981 | World Int. Prop. O. |

Primary Examiner—C. Fred Rosenbaum
Assistant Examiner—John D. Ferros
Attorney, Agent, or Firm—Frishauf, Holtz, Goodman & Woodward

[57] ABSTRACT

A medical device has an outer cylinder and an outer cylinder hub which has a hollow portion communicating with the interior of the outer cylinder and fixed to a proximal portion of the outer cylinder. An inner cylinder is provided which can be detachably inserted into the outer cylinder through the hollow portion of the outer cylinder hub. An inner cylinder hub is provided which has a hollow portion communicating with the interior of the inner cylinder, can be fitted within the outer cylinder hub, and is connected to a proximal portion of the inner cylinder. Means is arranged between the outer and inner cylinder hubs, for preventing relative axial movement of the outer and inner cylinder hubs when the inner cylinder is inserted into the outer cylinder and the inner cylinder hub is fitted into the outer cylinder hub. Means is arranged between the outer and inner cylinder hubs, for preventing relative circumferential rotation of the outer and inner cylinder hubs.

5 Claims, 10 Drawing Figures

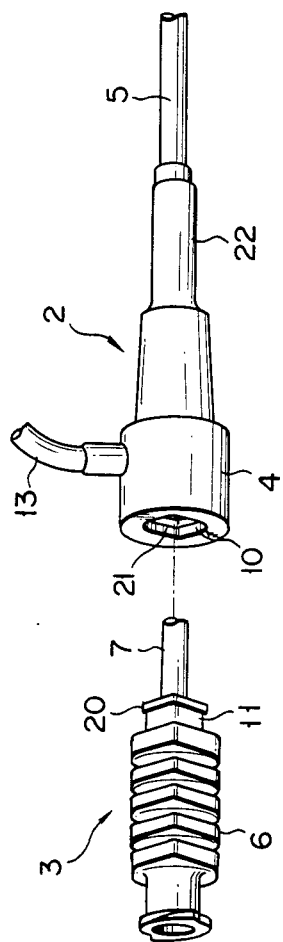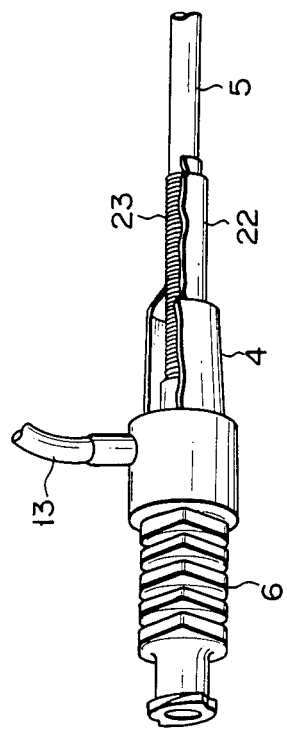
FIG. 8A
FIG. 8B

MEDICAL DEVICE

BACKGROUND OF THE INVENTION

I. Field of the Invention

The present invention relates to a medical device for introducing a catheter into a blood vessel or the like of a patient.

II. Description of the Prior Art

A medical device called a catheter introducer is known as a device for percutaneous insertion of a catheter into a blood vessel. A catheter introducer is composed of a sheath portion having a sheath and a sheath hub, and a dilator portion having a tube and a dilator hub. When such a catheter introducer is used, the dilator portion is set in the sheath portion and the dilator and sheath portions are inserted into a blood vessel via a guide wire.

The dilator and sheath portions can be easily inserted when they are simultaneously rotated during insertion. In a conventional catheter introducer, no means for simultaneously rotating the sheath and dilator portions is included. In such a conventional catheter introducer, in order to insert the assembly of sheath and dilator portions into a blood vessel while preventing rotation between the sheath and dilator portions, the hubs in the two portions must either be clamped together, or the tube of the dilator portion must be firmly clamped at a position above the sheath of the sheath portion so as to simultaneously rotate the two portions, thus resulting in a complex procedure. Yet, even if such a complex operation is performed, only the sheath portion can be inserted, the dilator portion being impeded by resistance of tissue or the like.

SUMMARY OF THE INVENTION

It is an object of the present invention to provide a medical device, i.e., a catheter introducer, which can easily insert dilator and sheath portions into a blood vessel while simultaneouly rotating them in an identical direction.

According to the present invention, there is provided a medical device comprising an outer cylinder; an outer cylinder hub which has a hollow portion communicating with the interior of the outer cylinder and fixed to a proximal portion of the outer cylinder; an inner cylinder which can be detachably inserted into the outer cylinder through the hollow portion of the outer cylinder hub; an inner cylinder hub which has a hollow portion communicating with the interior of the inner cylinder, can be connected to the outer cylinder hub, and is fixed to a proximal portion of the inner cylinder; means, arranged between the outer and inner cylinder hubs, for preventing relative axial movement of the outer and inner cylinder hubs when the inner cylinder is inserted into the outer cylinder and the inner cylinder hub is connected to the outer cylinder hub; and means, arranged between the outer and inner cylinder hubs, for preventing relative circumferential rotation of the hubs.

Preferably, the means for preventing circumferential relative movement includes a recess and a projection formed in the outer and inner hubs, respectively. The means for preventing axial movement and circumferential relative rotation preferably includes a female polygonal cylinder defining the hollow portion of the outer cylinder hub, and a male polygonal prism of the inner cylinder hub capable of being fit within the polygonal cylinder.

BRIEF DESCRIPTION OF THE DRAWINGS

FIGS. 8A, 8B and 9 are perspective views showing another embodiment of a medical device of the present invention.

DETAILED DESCRIPTION OF THE PREFERRED EMBODIMENTS

The preferred embodiment of a medical device according to the present invention will be described below.

Figure 4:
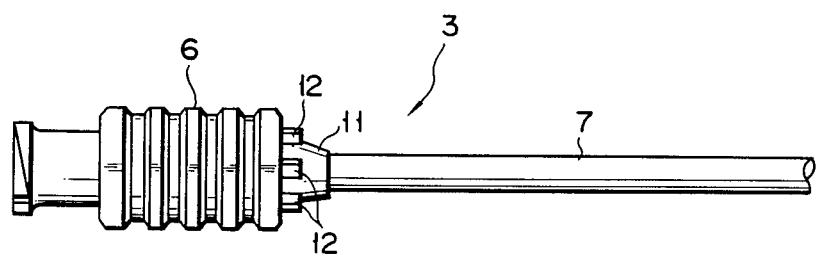
FIG. 4 is a side view of a rod member in the medical device of the present invention.

A medical device 1 (FIG. 1) of the present invention includes a medical device main body 2 (FIG. 2) and a rod member 3 (FIG. 4). The main body 2 corresponds to the sheath portion, and the rod member 3 corresponds to the dilator portion of a catheter introducer.

Figure 2:
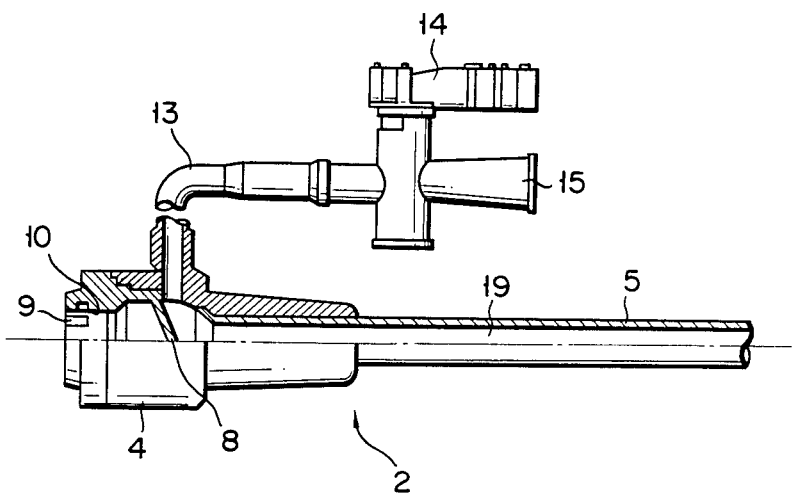
FIG. 2 is a partial sectional view of the main body of the medical device of the present invention.

The medical device main body 2 has a hub 4 and a sheath 5 having its proximal portion fixed and supported by the hub 4, as shown in FIG. 2. The hub 4 and the sheath 5 have a through path 19 for receiving a tube 7 of the rod member 3.

A valve 8 is mounted, preferably, in the portion of the through path 19 in the hub 4. The valve 8 serves to prevent reverse flow of blood when the medical device main body 2 is inserted into a blood vessel.

As shown in FIG. 4, the rod member or dilator portion 3 has a hub 6 and a tube 7 fixed and supported thereby. The dilator portion 3 is inserted in and assembled with the main body 2 shown in FIG. 2. With this arrangement, when the main body 2 and the rod member 3 are percutaneously inserted into a blood vessel, they rotate relative to each other and, as such, may not lend themselves to easy insertion, as described above.

In view of this problem, according to the present invention a mechanism for preventing relative rotation between the main body 2 and the dilator portion 3 is incorporated. The relative rotation preventing mechanism can have various constructions between the main body 2 and the dilator portion 3. In a typical example, to be described below, a groove is formed in one of the main body 2 and the dilator portion 3, and a rib, capable of being fitted within the groove, is formed in the other. The two members are taper fitted to prevent relative rotation and axial separation therebetween. According to the present invention, other constructions may be adopted including those to be described below.

Figure 3:
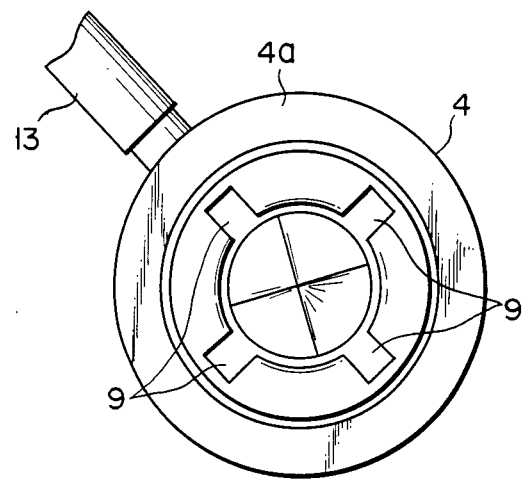
FIG. 3 is a partial end view of the main body shown in FIG. 2, as viewed from the left side.

As shown in FIGS. 2 and 3 in particular, at the rear end of the hub 4 of the main body 2, the inner wall of the hub 4 defining the rear end of the through path 19 constitutes a female taper fitting portion 10. At least one groove 9 (four grooves in FIG. 3) is formed at part of the fitting portion 10 in, preferably, a symmetrical configuration. When the grooves 9 are symmetrical, assembly is easy.

The main body 2 is connected at its hub 4 portion to a three port connection valve 14 through a side tube 13 communicating with the hub 4. This valve 14 can be operated to replenish a liquid through a lure taper port 15.

As shown in FIG. 4, at the side of the dilator portion, a male taper fitting portion 11 is formed at the distal end side of the dilator hub 6, and can be fitted within the fitting portion 10 of the sheath portion 2. Ribs 12 for fitting within the grooves 9 of the sheath portion 2 are formed on the fitting portion 11.

Figure 1:
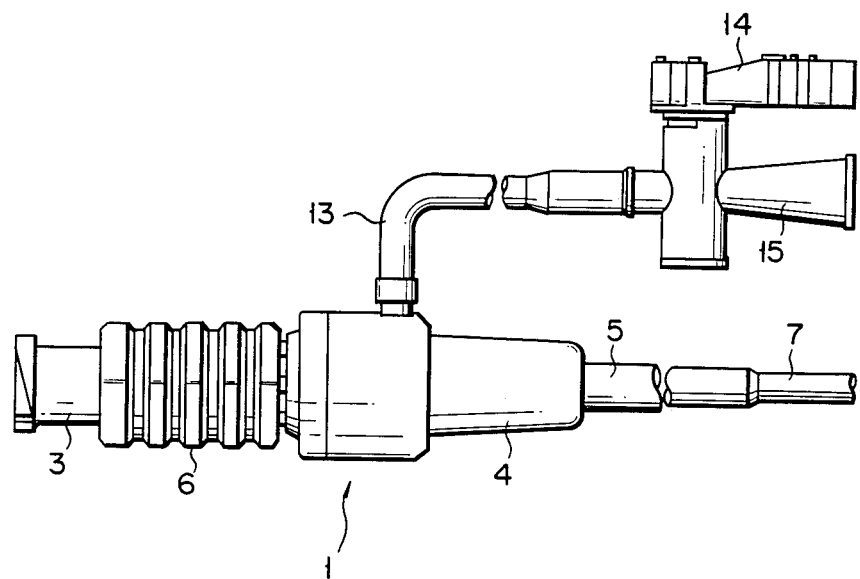
FIG. 1 is a side view of an assembled medical device of the present invention.

FIG. 1 shows a state wherein the sheath portion 2 in FIG. 2 is assembled with the dilator portion 3 shown in FIG. 4. Assembly can be performed as follows. The tube 7 of the dilator portion 3 is inserted into the through path 19 in the hub 4 and the sheath 5 from the side of the hub 4 of the sheath portion 2. The hub 6 of the dilator portion 3 and the hub 4 of the sheath portion 3 are then fit together. At this time, the fitting portion 11 of the dilator portion 3 is fitted within the fitting portion 10 of the sheath portion 3 so as to prevent axial relative movement between the dilator and sheath portions 3 and 2. Similarly, the ribs 12 of the dilator portion 3 are tightly fitted into the grooves 9 of the sheath portion 2 and locked so as to prevent circumferential relative rotation between the dilator and sheath portions 3 and 2.

Figure 9:
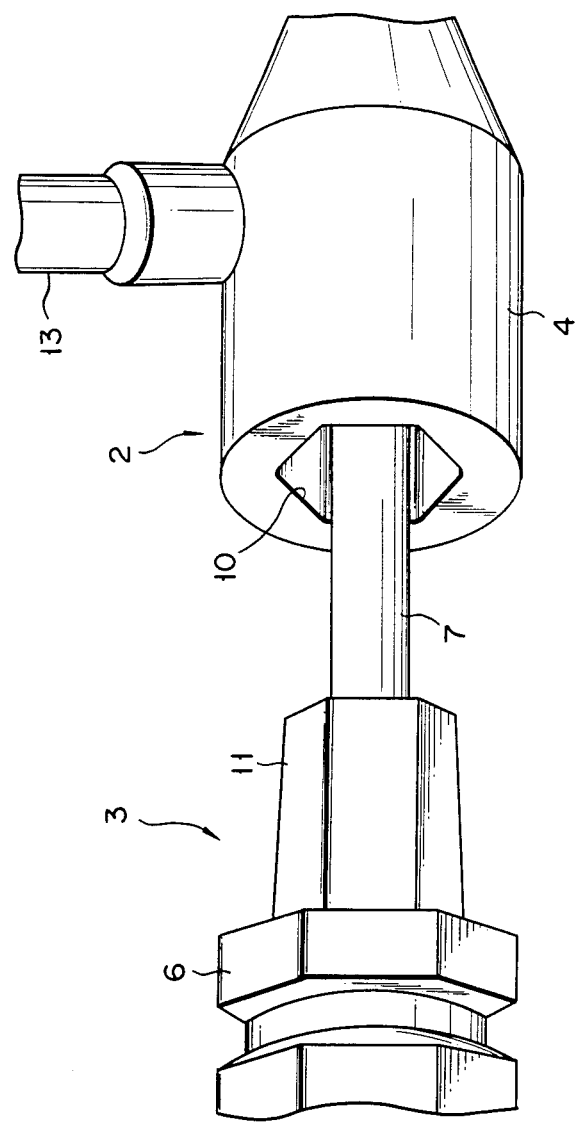

FIGS. 8 and 9 show another arrangement of a mechanism for preventing axial displacement and circumferential rotation.

In the arrangement shown in FIG. 8A, fitting portions 11 and 10 of a rod member 3 and a medical device main body 2 have hexagonal sections to prevent relative rotation therebetween. Ribs 20 and 21 on the fitting portions 11 and 10 engage with each other so as to prevent axial displacement therebetween. The ribs 20 and 21 need be formed to engage with at least parts of the fitting portions. The rib 20 slips over and positions beyond the rib 21, thus preventing the axial movement. It is preferred to form three ribs, instead of the angular rib 20, on the periphery of the portion 11, spaced apart from each other at angular intervals of 120° when the portion 11 is of hexagonal shape. This configuration of the ribs facilitates the slipping-over and pulling-out operations. (FIG. 8B shows the state wherein the fitting portions 11 and 10 are fit together.) In the arrangement in FIG. 8B, a shrinkage tube 22 a bending spring 23 are also shown.

In the arrangement shown in FIG. 9, a male fitting portion 11 of a rod member 3, and a female fitting portion 10 of a medical device main body 2 are tapered and have hexagonal sections. Thus, the fitting portions prevent axial displacement between the portions by taper fitting, and also prevent rotation by hexagonal section fitting.

As described above, the sections of fitting portions of the rod member 3 and the medical device main body 2 need not be circular but can be various shapes, including polygons such as hexagons or ellipses.

The method of using the medical device of the present invention will be described with reference to FIGS. 5 to 7.

Figure 5:
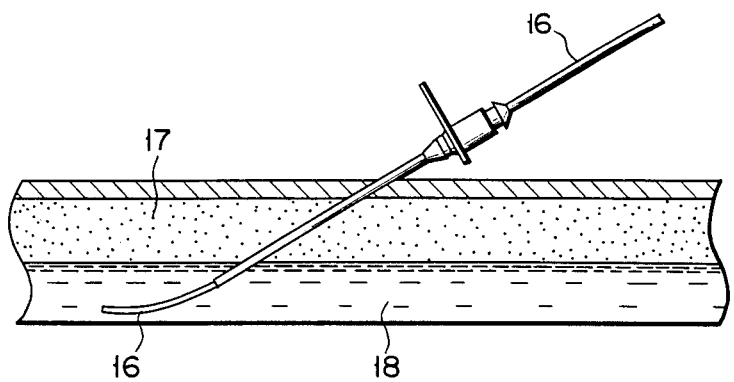
FIGS. 5, 6 and 7 are diagrams for explaining the operation for inserting a medical device of the present invention into a blood vessel.
Figure 6:
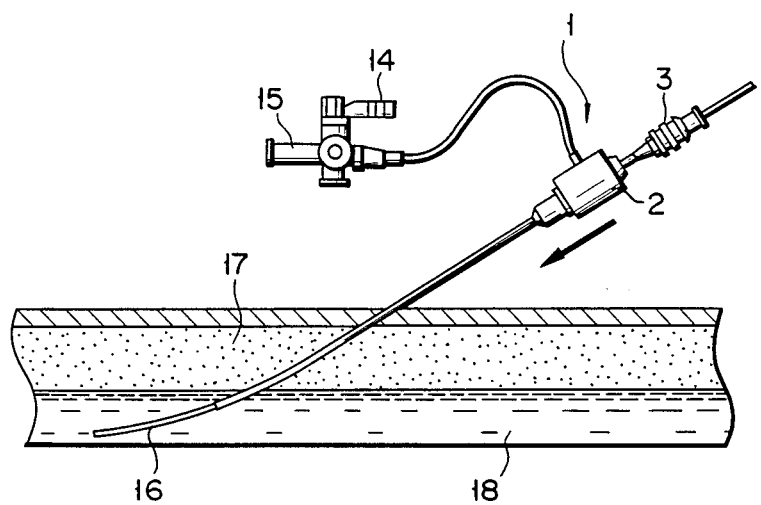

A guide wire 16 is inserted into a blood vessel 18 through a subcutaneous tissue 17 by a suitable method such as the Seldinger method (FIG. 5). Then, the medical device main body 1, obtained by assembling the sheath portion (medical device main body) 2 shown in FIG. 2 and the dilator portion (rod member) 3 shown in FIG. 4 so as to prevent axial movement and circumferential rotation as shown in FIG. 1, is inserted into a blood vessel 18 by inserting the guide wire 16 into the tube 7, the sheath 5 and the through hole in the hubs 4 and 6 (FIG. 6).

In this process, insertion into the blood vessel can be easily performed when the hub 6 of the dilator portion 3 is rotated during insertion. In contrast, insertion of the main body 1 cannot be performed easily with a conventional device, since the conventional device does not include a mechanism for preventing relative rotation between the dilator and sheath portions, as described above.

In the medical device of the present invention, relative rotation between the dilator and sheath portions 3 and 2 is prevented by the ribs 12 and grooves 9. In addition, axial movement between the portions 3 and 2 is prevented by a fitting force obtained either by the female and male fitting portions 10 and 11, or by the arrangement shown in FIG. 8 or 9. Therefore, insertion of the medical device main body 1 into the blood vessel 18 through means of the guide wire 16 is facilitated.

Figure 7:
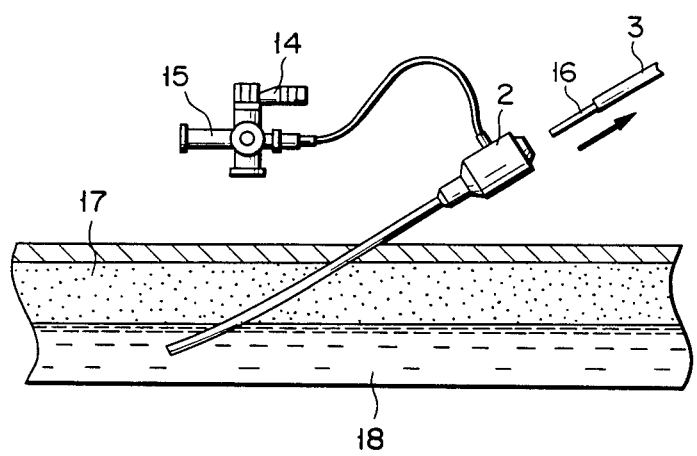

Subsequently, the sheath portion 6 is left in the blood vessel 18, and the guide wire 16 and the dilator portion 3 are pulled out (FIG. 7).

The catheter can be easily inserted into the blood vessel 18 through the indwelling sheath portion 2. Since the sheath portion 2 has a check valve 8, reverse flow of blood is prevented. If required, suction of a thrombus or injection of a physiological saline solution can be performed through the lure taper port 15 of the sheath portion 2 before or after insertion of the catheter.

In the medical device of the present invention, a female taper fitting portion and a groove are formed at the side of a medical device main body, and a male fitting portion and a rib are formed at the side of a rod member. When the medical device main body and the rod member are assembled, the taper fitting portions of the two members are tightly fit together so as to prevent axial relative movement or separation of the two members. At the same time, the groove and rib of the two members are tightly fit together so as to prevent relative rotation between the two members. A similar effect can be obtained if the means for preventing axial movement is a recess and a projection formed, respectively, in the fitting surfaces of the outer and inner cylinder hubs, while the means for preventing circumferential relative rotation is a female polygonal cylinder defining the hollow portion of the outer cylinder hub, and a male polygonal prism of the inner cylinder hub to be fitted therewith.

When the resultant assembly is inserted into a blood vessel, as described with reference to FIGS. 5 to 7, a suitable portion of the assembly, such as the hub of the rod member, is clamped such that the assembly is inserted while applying a rotational force around the guide wire. The insertion operation which, conventionally, has been complex is, through application of the invention, made easy.

What is claimed is:

1. A medical device, comprising:
   a first elongated hollow cylindrical member;
   a first hollow hub member fixed to a proximal end of said first cylindrical member, the interior of said first hub member communicating with the interior of said first cylindrical member;

a second elongated hollow cylindrical member detachably insertable into said first cylindrical member;

a second hollow hub member fixed to a proximal end of said second cylindrical member, the interior of said second hub member communicating with the interior of said second cylindrical member;

first means for preventing relative axial movement of said first and said second cylindrical members, including a first annular rib formed on the outer surface of said second hub member, and a second annular rib formed on the inner surface of said first hub member, said first rib being located to position beyond said second rib to prevent said axial movement when said second cylindrical member is inserted into said first cylindrical member; and second means for preventing relative circumferential rotation of said first and said second cylindrical members, including a female polygonal prism surface defining the inner surface of said first hub member, and a male polygonal prism surface defining the outer surface of said second hub member, said male prism being fitted into said female prism to prevent said rotation when said second cylindrical member is inserted into said first cylindrical member.

2. A medical device, comprising:

a first elongated hollow cylindrical member;

a first hollow hub member fixed to a proximal end of said first cylindrical member, the interior of said first hub member communicating with the interior of said first cylindrical member;

a second elongated hollow cylindrical member detachably insertable into said first cylindrical member;

a second hollow hub member fixed to a proximal end of said second cylindrical member, the interior of said second hub member communicating with the interior of said second cylindrical member;

first means for preventing relative axial movement of said first and said second cylindrical members, including a male tapered surface defining the outer surface of said second hub member, and a female tapered surface defining the inner surface of said first hub member, said male tapered surface being fitted into said female tapered surface to prevent said axial movement when said second cylindrical member is inserted into said first cylindrical member; and second means for preventing relative circumferential rotation of said first and said second cylindrical members, including a female polygonal prism surface defining the inner surface of said first hub member, and a male polygonal prism surface defining the outer surface of said second hub member, said male prism being fitted into said female prism to prevent said rotation when said second cylindrical member is inserted into said first cylindrical member.

3. A catheter introducer, comprising:

a sheath including a first elongated hollow cylindrical member and a first hollow hub member fitted to a proximal end of said first cylindrical member;

a dilator including a second elongated hollow cylindrical member detachably insertable into said first cylindrical member, and a second hub member fixed to a proximal end of said second cylindrical member, said second cylindrical member being adapted to guide a catheter therethrough;

said first hub member including a female polygonal inner surface and a first annular rib;

said second hub member including a male polygonal outer surface and a second annular rib; and said male polygonal outer surface being formed to fit said female polygonal inner surface and said second rib being located to position beyond said first rib, so that relative axial movement and relative rotation of said sheath and said dilator are prevented when said second cylindrical member is inserted into said first cylindrical member.

4. A catheter introducer, comprising:

a sheath including a first elongated hollow cylindrical member and a first hollow hub member fitted to a proximal end of said first cylindrical member;

a dilator including a second elongated hollow cylindrical member detachably insertable into said first cylindrical member, and a second hub member fixed to a proximal end of said second cylindrical member, said second cylindrical member being adapted to guide a catheter therethrough;

said first hub member having a female tapered polygonal inner surface;

said second hub member having a male tapered polygonal outer surface; and said male tapered polygonal outer surface being formed to fit said female tapered polygonal inner surface, so that relative axial movement and relative rotation of said sheath and said dilator are prevented when said second cylindrical member is inserted into said first cylindrical member.

5. A medical device, comprising:

a first elongated hollow cylindrical member;

a first hollow hub member fixed to a proximal end of said first cylindrical member, the interior of said first hub member communicating with the interior of said first cylindrical member;

a second elongated hollow cylindrical member detachably insertable into said first cylindrical member;

a second hollow hub member fixed to a proximal end of said second cylindrical member, the interior of said second hub member communicating with the interior of said second cylindrical member;

means for preventing relative movement of said first and said second cylindrical members, including a first annular rib formed on the outer surface of said second hub member, and a second annular rib formed on the inner surface of said first hub member, said first and said second ribs being located to position beyond each other to prevent said axial movement when said second cylindrical member is inserted into said first cylindrical member; and said first and said second hub members having tapered polygonal fitting surfaces, and being taper-fitted with each other to prevent relative circumferential rotation of said first and said second cylindrical members when said second cylindrical member is inserted into said first cylindrical member.

* * * * *